(12) United States Patent
Griswold

(10) Patent No.: US 8,532,790 B2
(45) Date of Patent: Sep. 10, 2013

(54) SLIDABLE FIXATION DEVICE FOR SECURING A MEDICAL IMPLANT

(75) Inventor: Erik Griswold, Mill Valley, CA (US)

(73) Assignee: Medtronic, Inc., Minneapolis, MN (US)

( * ) Notice: Subject to any disclaimer, the term of this patent is extended or adjusted under 35 U.S.C. 154(b) by 395 days.

(21) Appl. No.: 12/759,173

(22) Filed: Apr. 13, 2010

(65) Prior Publication Data

US 2011/0251660 A1     Oct. 13, 2011

(51) Int. Cl.
*A61N 1/00* (2006.01)

(52) U.S. Cl.
USPC ......................................... 607/126

(58) Field of Classification Search
USPC ................................. 607/126, 128
See application file for complete search history.

(56) References Cited

U.S. PATENT DOCUMENTS

| | | | |
|---|---|---|---|
| 4,913,164 A * | 4/1990 | Greene et al. | 607/126 |
| 5,492,119 A * | 2/1996 | Abrams | 600/375 |
| 7,617,007 B2 | 11/2009 | Williams | |
| 2004/0059404 A1 * | 3/2004 | Bjorklund et al. | 607/126 |
| 2004/0064158 A1 | 4/2004 | Klein | |
| 2004/0249431 A1 * | 12/2004 | Ransbury et al. | 607/126 |
| 2005/0033395 A1 * | 2/2005 | Seifert et al. | 607/126 |
| 2005/0288596 A1 | 12/2005 | Eigler | |
| 2007/0239248 A1 * | 10/2007 | Hastings et al. | 607/127 |
| 2007/0293925 A1 * | 12/2007 | Zarembo et al. | 607/126 |
| 2008/0021532 A1 * | 1/2008 | Kveen et al. | 607/115 |
| 2009/0082828 A1 | 3/2009 | Ostroff | |

* cited by examiner

*Primary Examiner* — Niketa Patel
*Assistant Examiner* — Minh Duc Pham
(74) *Attorney, Agent, or Firm* — Reed A. Duthler; Stephen W. Bauer

(57) ABSTRACT

A fixation device for retaining a leadless medical implant to tissue includes an annular collar and an array of self-expanding tines extending from the collar. When deployed, the annular collar encircles the implant and the tines are preset to splay outwardly from the implant to grab body tissue and anchor the implant at a treatment site. The implant and fixation device are contained within a sheath for delivery to the treatment site and a pushing force is applied to a pusher of the delivery system to distally advance the fixation device relative to the implant and deploy the tines. A distal end of the implant having an electrode may form a distal tip of the delivery system, and a potential implantation site may be tested prior to deployment of the fixation device to allow for easy repositioning of the implant if the potential implantation site is determined to be unacceptable.

20 Claims, 3 Drawing Sheets

SLIDABLE FIXATION DEVICE FOR SECURING A MEDICAL IMPLANT

FIELD OF THE INVENTION

The invention relates to a fixation device for securing a medical implant to tissue of the heart.

BACKGROUND OF THE INVENTION

Medical implants such as leadless stimulators or sensors may be surgically, or in some instances, percutaneously delivered and implanted within tissue of the heart. The potential for detachment of a leadless stimulator or sensor from an implantation site represents a serious and possibly life-threatening event. For example, a leadless pacemaker that becomes dislodged from an implantation site in the right ventricle of the heart can exit the heart via the pulmonic valve and lodge in the lung. Thus, secure fixation of leadless implants is extremely important for successful operation of the implant as well as for the safety of the patient.

In order to secure the implant to tissue at the implantation site, the implant may include anchoring structure at a distal end thereof that must be screwed or otherwise engaged with tissue at the implantation site. The anchoring structure is typically housed within a distal end of a retractable delivery sheath or other covering during delivery of the implant to avoid injury to the patient as the implant is brought to an implantation site. The anchoring structure is typically deployed to lodge within the tissue by being distally slid and/or rotated relative to the distal end of the delivery sheath. The delivery sheath is often a somewhat rigid tubular structure and typically includes an open blunt end that may scrape or otherwise cause injury to the patient as the delivery sheath is being tracked to the implantation site. In the case of a leadless pacemaker, such a distally placed anchoring structure makes it difficult or impossible to test the implantation site for responsiveness to determine whether that area of the heart will accept pacing pulses until after the full deployment of the anchoring structure such that an electrode of the pacemaker makes contact with the heart. In addition, if the implantation site is determined to be unacceptable or less than optimal after deployment of the distal anchoring structure, it may be difficult or impossible to reposition the pacemaker without injury to the heart. Thus a need exists in the art for a delivery and anchoring apparatus and method for delivering and implanting a leadless implant in the heart that solves one or more of the deficiencies identified above.

BRIEF SUMMARY OF THE INVENTION

Embodiments hereof relate to a method of securing a medical implant to body tissue, particularly to heart tissue. The medical implant may be mounted within an outer sheath of a delivery system to be percutaneously delivered to an implantation site. The medical implant includes a fixation device slidably mounted thereon. The fixation device includes an annular collar and an array of self-expanding tines that distally extend from the collar, wherein the tines are constrained and substantially straightened by the outer sheath during delivery. When the medical implant is situated at the implantation site, the fixation device is distally advanced over the medical implant to distally extend the tines from the outer sheath into contact with body tissue. Once released from the constraint of the outer sheath, as the tines penetrate or otherwise engage body tissue they tend to splay outwardly from the medical implant and curve backwards toward the collar to retain the medical implant at the implantation site. In an embodiment hereof, a distal end of the implant includes an electrode that protrudes out of a distal end of the outer sheath to form a distal tip of the delivery system such that the electrode may be utilized for testing the implantation site for suitability prior to deploying the fixation device.

Embodiments hereof also relate to a system for percutaneously delivering a medical implant to an implantation site and securing the medical implant at the implantation site. The system includes an outer sheath having a lumen extending there through and a medical implant held within the outer sheath lumen at a distal end thereof. A distal end of the medical implant protrudes out of the outer sheath distal end to form a distal tip of the delivery system. The system also includes a fixation device having an annular collar and an array of self-expanding tines that distally extend from the collar and are preset to splay outwardly from the medical implant and curve backward toward the collar. The fixation device is positioned proximal of the distal end of the delivery system during delivery and, if applicable, during the testing of the implantation site. The fixation device is slidably mounted on the medical implant such that the fixation device may be distally advanced over the medical implant to deploy the tines from a delivery configuration, in which the tines are constrained and substantially straightened by the outer sheath, to an expanded configuration, in which the tines are released from the outer sheath and tend to assume their preset shape.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of placement of a leadless pacemaker for treatment of the heart, the invention may also be adapted for use in delivering and implanting medical sensors or stimulators to other areas of a patient's body where it is deemed useful. Furthermore, there is no intention to be bound by any expressed or implied theory presented in the preceding technical field, background, brief summary or the following detailed description.

Figure 1:
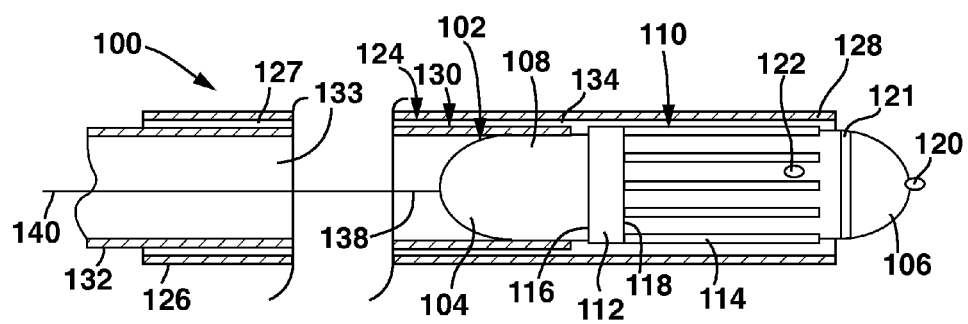
FIG. 1 is a side view in partial section of an implant delivery system, wherein tines of a slidable fixation device are constrained in a delivery configuration.
Figure 2:
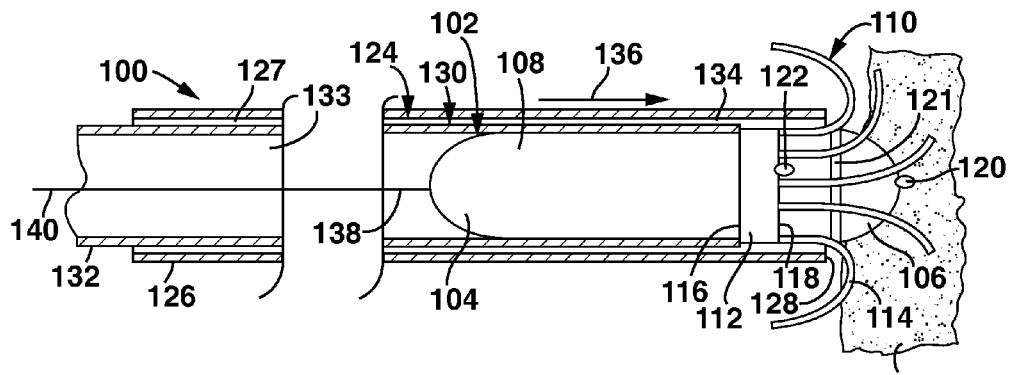
FIG. 2 is a side view in partial section of the implant delivery system of FIG. 1, wherein the tines of the slidable fixation device are extended in a deployed configuration.

Embodiments hereof relate to systems and methods for delivering and securing or anchoring a medical implant within body tissue, such as tissue of the heart. FIGS. 1 and 2 are side views in partial section of an implant delivery system 100 for delivering and implanting implant 102. In embodiments described herein, implant 102 is a leadless pacing system of the type described in U.S. Pat. No. 5,193,539 to Shulman et al. In the instant disclosure, implant 102 may be delivered and implanted percutaneously in the heart in a minimally invasive procedure via delivery system 100. For purposes of describing the invention hereof, only the basic structure of implant 102 is described herein. Particularly, implant 102 includes at least two electrodes and a generally cylindrical, capsule-shaped housing 108 that hermetically encloses the pacing system's electrical components, including a wireless communication system and an internal power source. A first electrode 120 extends distally from a distal end 106 of implant 102 and a second electrode 121 having a ring-shape to encircle housing 108 is positioned just proximal of implant distal end 106. Electrodes 120, 121 are connected to the electrical components within housing 108 with feed-through ports (not shown). In an alternative embodiment (not shown), a second electrode may comprise an entire portion of a titanium housing that is separated from a distal tip electrode by an insulating ring. When implanted at an implantation site in the heart, first distal electrode 120 of implant 102 is in intimate contact with the heart wall including the myocardium, the thickest and middle layer of the tissue. Implant 102 is sized to be tracked through the vasculature, i.e., through a femoral vein, a femoral artery, or the subclavian, within delivery system 100 and may have a diameter or transverse dimension of up to 9 mm. In accordance with embodiments hereof, implant 102 may be delivered through the vasculature to be implanted at a septum of the heart or at the apex of the right ventricle. In other embodiments, implant 102 may be implanted within another heart chamber on either side of the heart. Although implant 102 is described herein as a leadless pacing system, in other embodiments hereof delivery system 100 may be used to deliver and implant other medical device that are configured to be secured within body tissue, such as a sensor device or another type of stimulator device, and may or may not be "leadless" or self-contained.

Figure 3:
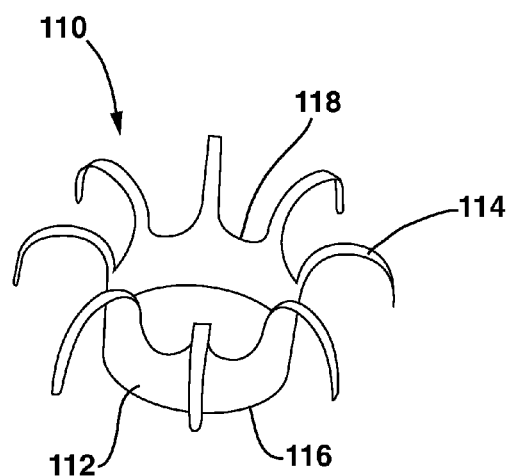
FIG. 3 is a perspective illustration of the slidable fixation device of FIG. 1 removed from the implant delivery system.

Implant 102 is retained in heart tissue via a fixation device 110, which is shown in a delivery configuration in FIG. 1 and an expanded, deployed configuration in FIG. 2. With reference to FIG. 3, fixation device 110 includes an annular collar 112 for encircling and sliding along generally cylindrical implant housing 108 and an array of prongs or tines 114 that extend from an edge 118 of collar 112. Fixation device 110 is formed of a shape memory material and tines 114 are preset to splay outwardly from implant 102 and to curve backwards toward collar 112. In an embodiment, fixation device 110 is formed from a self-expanding material including but not limited to spring temper stainless steel or a stress induced martensite "superelastic" material such as nitinol, a binary alloy of nickel and titanium. "Self-expanding" as used herein means that tines 114 of fixation device 110 have a mechanical memory to return to the expanded, deployed configuration shown in FIGS. 2 and 3 from the straightened delivery configuration shown in FIG. 1. Mechanical memory may be imparted to tines 114 of fixation device 110 by thermal treatment to achieve to set a shape memory in a susceptible metal alloy, such as nitinol or a spring temper stainless steel. In an alternate embodiment, tines 114 may be separately formed of a shape memory material and attached to collar 112 formed of a different material via any suitable mechanical method. Although fixation device 110 is shown in the embodiment of FIG. 3 with eight tines, it will be apparent to those of ordinary skill in the art that fixation device 110 may include more or fewer tines. As noted above, collar 112 is slidingly disposed over housing 108 rather than being longitudinally fixed relative thereto. In the illustrated embodiment, inner diameter of collar 112 is only slightly smaller than an outer diameter of housing 108 such that although collar 112 is slidable along housing 108 with the application of a pushing force, there is a light interference fit between collar 112 and housing 108 for reasons that will be described below.

Implant delivery system 100 includes an outer containment sheath 124 having a proximal end 126, a distal end 128, and a lumen 127 extending therethrough and an inner pusher 130 having a proximal end 132, a distal end 134, and a lumen 133 extending there through. Pusher 130 is concentrically disposed within containment sheath 124 and is sized to slidably extend through lumen 127 thereof. Containment sheath 124 and pusher 130 may be formed from tubes or tubing of a flexible polymeric material such as polyethylene terephthalate (PET), polyamide, polyethylene, polyethylene block amide copolymer (PEBA), or combinations thereof. Implant 102 is at least partially contained within a distal portion of containment sheath lumen 127 with a proximal edge 116 of fixation device collar 112 positioned toward proximal end 104 of housing 108 to be contactable by distal end 134 of pusher 130 and with tines 114 of fixation element 110 distally extending in a straightened configuration against implant housing 108. As will be explained in more detail herein, containment sheath 124 serves to constrain tines 114 of fixation device 110 in the delivery configuration of FIG. 1 and pusher 130 serves to distally advance or slide fixation device 110 over implant 102 and relative to containment sheath 124 in order to release tines 114 into the deployed configuration of FIG. 2. In an embodiment, proximal end 104 of housing 108 may be releasably attached to an optional tether or core wire 138 that extends through pusher lumen 133. Proximal ends 126, 132, 140 of containment sheath 124, pusher 130, and tether 138, respectively, each extend proximally outside of the patient's body such that they may be manipulated by a clinician and one or more of the proximal ends may include a handle or knob (not shown) in order to facilitate securing a longitudinal position or sliding movement thereof.

When loaded within implant delivery system 100 for delivery, distal end 106 of implant 102 distally protrudes or extends from distal end 128 of containment sheath 124 to form a distal tip of implant delivery system 100, as illustrated in FIGS. 1, 4, 6 and 7. In the illustrated examples, the exposed portion of implant distal end 106 may have a smooth rounded profile such that implant delivery system 100 may be safely tracked through a patient's vasculature. As noted above electrode 120 extends distally from implant distal end 106 such that when implant 102 is tracked to and positioned at a potential implantation site, electrode 120 may be contacted with the implantation site to test the acceptability thereof prior to deployment of fixation device 110 and implant 102. More particularly, electrode 120 functions to continuously measure impedance in order to sense electrical contact with heart tissue such that once electrode 120 is in electrical contact with heart tissue, a test electrical pulse may be delivered via electrode 120 to test the responsiveness of the potential implantation site. If the potential implantation site accepts or otherwise responds appropriately to the test electrical pulse, the site is confirmed as the implantation site and tines 114 of fixation device 110 may be deployed to secure implant 102 at the implantation site. If the potential implantation site does not accept the test electrical pulse or is otherwise determined not to be acceptable, the site may be rejected and implant 102 may be moved to another potential implantation site and the testing procedure repeated until an acceptable implantation site is confirmed. Accordingly, implant delivery system 100 permits potential implantation sites to be tested without fixing implant 102 into heart tissue and implant 102 can be easily repositioned without damaging the body tissue if the sites are not optimal.

In an alternative embodiment (not shown), when loaded within implant delivery system 100 for delivery, distal end 106 of implant 102 may be recessed within distal end 128 of containment sheath 124. When implant 102 is tracked to and positioned at a potential implantation site, electrode 120 may be projected distally from implant distal end 106 to contact the implantation site to test the acceptability thereof prior to deployment of fixation device 110 and implant 102. As in the embodiment described above, if the potential implantation site does not accept the test electrical pulse or is otherwise determined not to be acceptable, the site may be rejected and implant 102 may be withdrawn into the distal end 128 of containment sheath 124 and moved to another potential implantation site. The advancement and testing procedure may be repeated until an acceptable implantation site is confirmed.

When an implantation site is confirmed and it is desired to deploy implant 102, distal end 134 of pusher 130 abuts proximal edge 116 of fixation device collar 112 to distally advance collar 112 in the direction of arrow 136 so that fixation device 110 slides along the outer surface of housing 108 and relative to containment sheath 124 to thereby release and deploy tines 114 from distal end 128 of containment sheath 124. Deployed tines 114 splay outwardly and distally from containment sheath 124 to engage trabeculae and/or penetrate other heart tissue.

In order to prevent fixation element 110 from sliding off housing 108 and to transfer some of the pushing force of pusher 130 to housing 108, a stop 122 protrudes from the outer surface of housing 108 to prevent farther distal advancement of collar 112. Collar 112 is prevented from sliding backward in a proximal direction due to the light interference fit between collar 112 and housing 108. In an alternate embodiment, housing 108 may include a notch or groove (not shown) thereon and collar 112 may include a tab (not shown) that catches within the notch when collar 112 is advanced distally to stop 122 to prevent collar 112 from sliding proximally on housing 108. In the alternative embodiment, collar 112 may have either a clearance fit or a light interference fit about the body of housing 108. Other variations of stops, detents, tabs, snap fits, notches and grooves may be used to secure collar 112 against either distal or proximal movement along housing 108 once implant 102 is in its deployed configuration. With continued force against pusher 130 and/or in combination with proximal retraction of containment sheath 124 relative thereto, implant 102 is deployed from delivery system 100. If present, tether 138 may be proximally tugged to assure implant 102 is secured at the implantation site by fixation device 110 prior to full deployment of implant 102. Once anchoring is confirmed, tether 138 may be disengaged from implant 102. For example, tether 138 may be attached to the proximal end of implant 102 by mating screw threads such that tether 138 may be rotated or turned about its own longitudinal axis in order to unscrew the threaded distal end and disengage tether 138 from implant 102. Implant delivery system 100 including tether 138, pusher 130 and containment sheath 124 may then be retracted and removed from the patient leaving implant 102 fixed at the implantation site.

As shown in FIG. 2, implant 102 is securely retained at the implantation site due to tines 114 of fixation device 110 being secured to the heart tissue 150. Further when tines 114 and implant 102 are deployed as described above, electrode 120 is pushed into the heart wall to be embedded therein. Ring electrode 121, serving as the indifferent electrode, is disposed on implant 102 at a distance from tip electrode 120 and may or may not be in contact with heart tissue depending on the depth to which implant 102 has penetrated tissue 150. Although implant 102 is illustrated in FIG. 2 as being deployed generally perpendicular to the heart wall, the disclosure is not so limited, and variations in the angle of deployment can also affect whether ring electrode 121 contacts heart tissue 150, as shown in FIG. 5.

Figure 4:
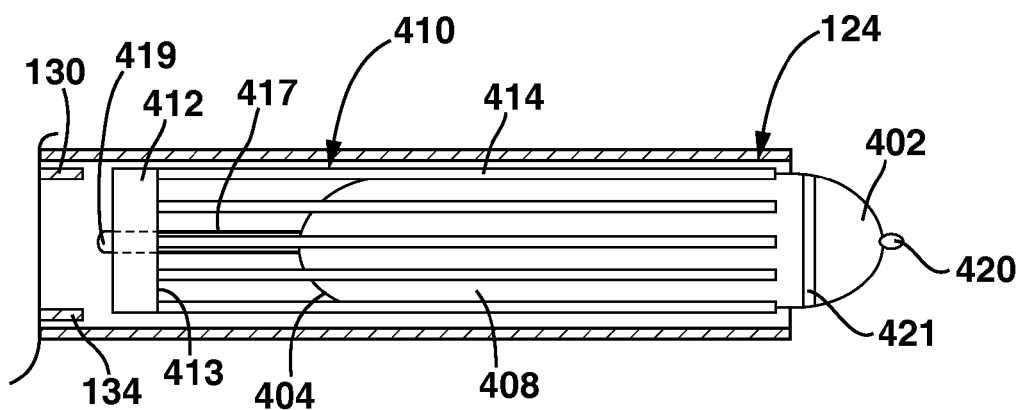
FIG. 4 is a side view in partial section of a distal portion of an implant delivery system according to another embodiment hereof, wherein tines of a slidable fixation device are constrained in a delivery configuration.
Figure 5:
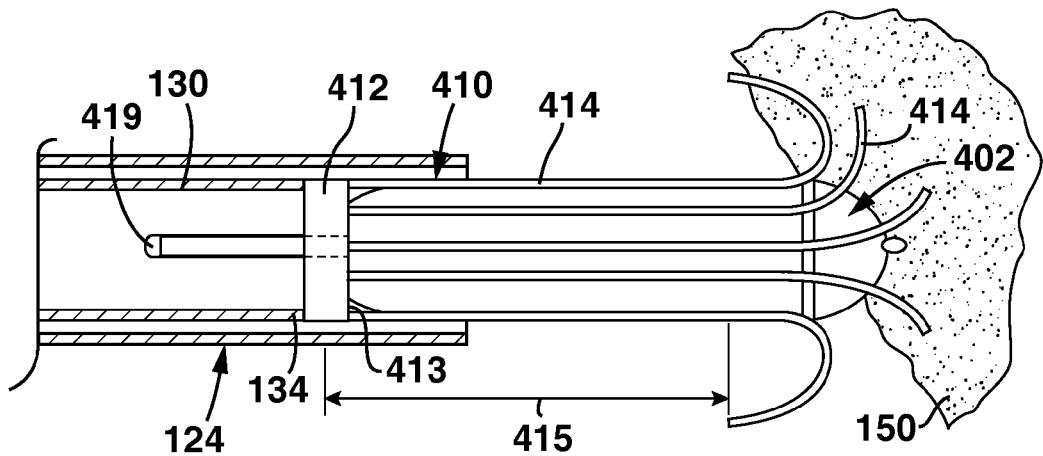
FIG. 5 is a side view in partial section of the distal portion of the implant delivery system of FIG. 4, wherein only distal portions of the tines of the slidable fixation device are extended in a deployed configuration.

FIGS. 4 and 5 illustrate a slidable fixation device 410 in accordance with another embodiment hereof with features of the remainder of the delivery system being the same as the previous embodiment. Fixation device 410 includes an annular collar 412 and an array of deployable tines 414 that extend from an edge 413 of annular collar 412. In the delivery configuration shown in FIG. 4, implant 402 is loaded within a distal portion of containment sheath 124 such that fixation device tines 414 are distally straightened by containment sheath 124 to lie against implant housing 408 and such that collar 412 is positioned proximal of housing proximal end 404. Fixation device 410 is of a shape memory material and tines 414 function similarly to tines 114 described above with an exception being that a substantial portion 415 of each tine 414 is preshaped to be straight and only a distal portion of each tine 414 is preset to radially curve backwards toward collar 412.

In an embodiment, implant 402 may include a proximally extending guide filament 417 having a stop 419 at the proximal end thereof. Collar 412 has an opening large enough to slidably receive guide filament 417, the opening being small enough to prevent stop 419 from entering. The movement of collar 412 between stop 419 and implant proximal end 404 is limited by the length of filament 417. Similar to electrode 120, electrode 420 may protrude from containment sheath 124 as shown in order to sense electrical contact with heart tissue and test the suitability of a potential implantation site.

After suitability of the implantation site is confirmed, fixation device 410 is distally advanced via pusher 130 to lock implant 402 in position. In an embodiment, guide filament 417 may be substantially wire-like to aid in guiding collar 412 and pusher 130 thereover during advancement of fixation device 410. In such an embodiment having a rigid filament 417, an inner pusher (not shown) can be slidably disposed within pusher 130 to abut and push against stop 419 to assist in advancing implant 402 against tissue 150.

In another embodiment, guide filament 417 may be substantially suture-like. In such an embodiment, flexible filament 417 may function as an extension of tether 138, which may be releasably secured to stop 419. Thus, pusher 130 may be guided over the combination of tether 138, stop 419 and filament 417. Tether 138 may also perform the function described above regarding tugging to test the security of fixation device 410 in tissue 150 before severing or otherwise disconnecting tether 138 from stop 419, or disconnecting filament 417 from implant 402. If flexible filament 417 and stop 419 are left attached to implant 402 after implantation thereof, then filament 417 may be loosely coiled between collar 412 and implant proximal end 404. Stop 419 may also serve as an attachment point for possible removal of implant 402, should such become necessary.

As shown in a partially deployed configuration in FIG. 5, portion 415 of each tine 414 remains straight and positioned against the outer surface of implant housing 408 when containment sheath 124 is removed. During deployment, tines 414 slide along generally cylindrical implant housing 408 while fixation device 410 is being advanced distally relative thereto by pusher 130. Advancement of fixation device 420 along housing 408 may stop when collar 412 abuts the rounded portion of housing proximal end 404 without collar 412 otherwise sliding distally along the generally cylindrical body of implant housing 408. Thus, this embodiment avoids the need for a precise fit, either clearance or interference between collar 412 and the generally cylindrical body portion of housing 408. Straight tine portions 415 may be preshaped so as to provide frictional engagement therealong with housing 408. Similar to the embodiments above, various stops, detents, tabs, snap fits, notches and grooves may be used to secure either collar 412 or tines 414 against either distal or proximal movement along housing 408 once implant 402 is in its deployed configuration. Once tines 414 have been secured within heart tissue, pusher 130 may then be held steady relative to implant 402 and containment sheath 124 as containment sheath 124 is proximally retracted to fully deploy implant 402. In this manner, fixation element 410, and more particularly the straight portions 415 of tines 414, envelope or encircle substantially the entire medical implant 402 in a basket-like arrangement to securely hold implant 402 against heart tissue when tines 414 are deployed at the implantation site.

Figure 6:
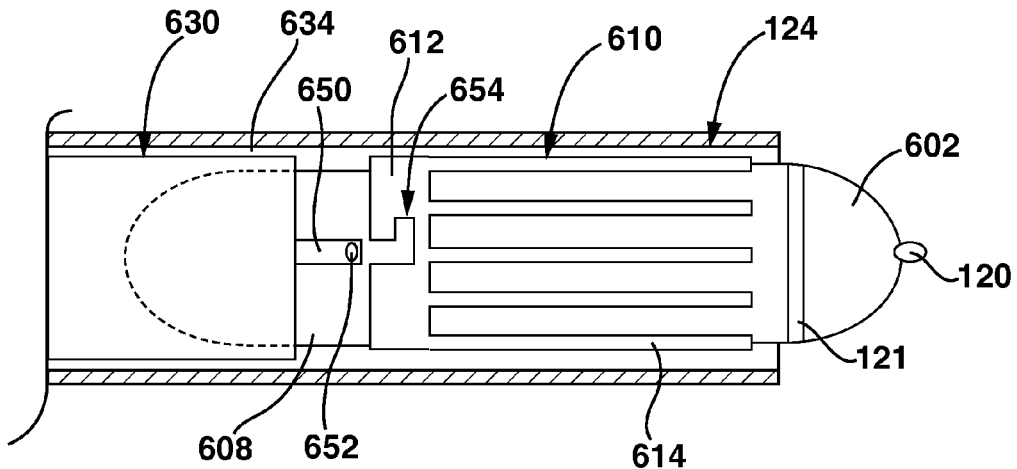
FIG. 6 is a side view in partial section of a distal portion of an implant delivery system according to another embodiment hereof in which a slidable fixation device is retractable, wherein the tines of the slidable fixation device are constrained in a delivery configuration.

According to another embodiment hereof, the slidable fixation device may be retractable such that the implant can be repositioned even after the tines are deployed. For example, it may be desirable to reposition the implant after the tines are deployed if the tines do not properly engage or entangle with the heart tissue or if the implantation site is subsequently determined to be less than optimal. FIG. 6 shows an embodiment in which pusher 630 and collar 612 of fixation device 610 are releasably coupled together using a version of a bayonet mount to enable proximal retraction of fixation device 610. In this embodiment, pusher 630 includes a tab 650 that distally extends from a distal end 634 of pusher 630. Tab 650 includes a radially extending protrusion 652 that is slidingly received in an L-shaped slot 654 formed within collar 612 of fixation device 610. The connection between pusher 630 and collar 612 transfers an applied force on pusher 630 to collar 612 to slide fixation device 610 along housing 608. If the applied force is a pushing force, then collar 612 is distally advanced along the outer surface of the implant to extend tines 614 out of containment sheath 124 to transform implant 602 into its deployed configuration. If the applied force is a pulling force, then collar 612 is proximally retracted over the outer surface of housing 608 to retract previously deployed tines 614 back into containment sheath 124 to their straightened delivery configuration. Pusher 630 may be engaged, disengaged or re-engaged with fixation device 610 using twist-and-push or twist-and-pull techniques known to those familiar with bayonet mounts.

Figure 7:
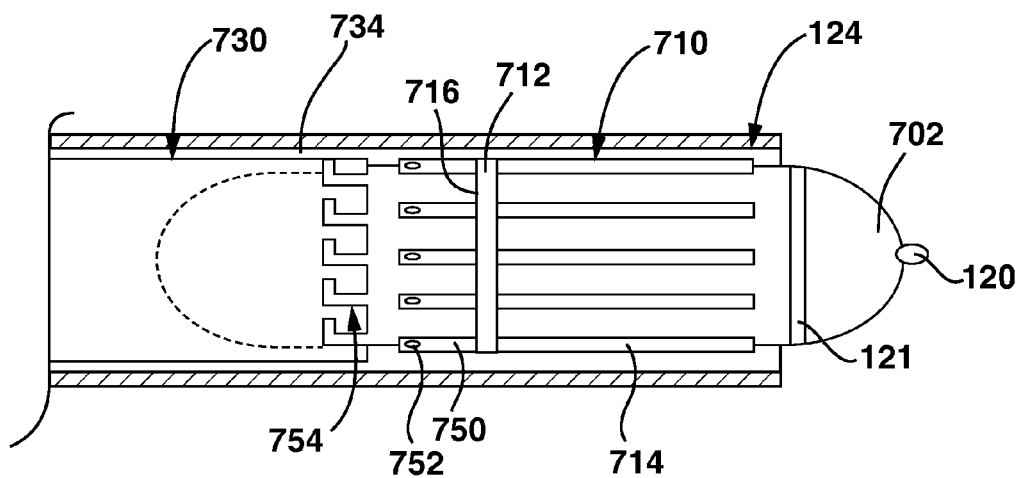
FIG. 7 is a side view in partial section of a distal portion of an implant delivery system according to yet another embodiment hereof in which a slidable fixation device is retractable, wherein the tines of the slidable fixation device are constrained in a delivery configuration.

In another embodiment as shown in FIG. 7, similar to the embodiment of FIG. 6, a pusher 730 and a collar 712 of a slidable fixation device 710 are connected by version of a bayonet mount using a plurality of L-shaped slots 754 formed within distal end 734 of pusher 730. A collar 712 of a slidable fixation device 710 includes a plurality of extensions or tabs 750 that extend from an edge 716 of collar 712. Each extension 750 includes a radially extending protrusion 752 that is slidingly received and catches within a corresponding L-shaped slot 754 in pusher 730 as described above with respect to FIG. 6. Protrusions 752 releasably couple pusher 730 to fixation device 710 so that pushing or pulling forces applied to pusher 730 are transmitted to fixation device 710 to distally extend or proximally retract tines 714, respectively, relative to implant 702.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of retaining a medical implant to body tissue, the method comprising the steps of:

positioning a medical implant mounted within a distal portion of an outer sheath of a delivery system at an implantation site, wherein the medical implant has a fixation device slidably mounted thereon that includes an annular collar and an array of self-expanding tines that extend from the collar and wherein the tines are constrained and substantially straightened against the medical implant by the outer sheath during positioning; and distally advancing the fixation device over the medical implant to release at least a portion of the tines from the outer sheath, wherein the at least a portion of the tines released from the outer sheath splay outwardly from the implant and radially curves backward towards the collar to engage with body tissue to retain the medical implant at the implantation site.

2. The method of claim 1, wherein the step of distally advancing the fixation device includes distally advancing an inner pusher slidably disposed within a lumen of the outer sheath to slide the collar of the fixation device over the medical implant.

3. The method of claim 2, wherein the pusher and the collar of the fixation device are releasably coupled together to enable proximal retraction of the fixation device.

4. The method of claim 1, wherein the step of distally advancing the fixation device includes advancing the collar until it contacts a radially-extending stop protruding from an outer surface of the medical implant.

5. The method of claim 1, wherein a rounded distal end of the medical implant protrudes out of a distal end of the outer sheath to form a distal tip of the delivery system while the delivery system is being tracked to the implantation site.

6. The method of claim 5, wherein the medical implant is a leadless pacemaker with an electrode extending from the distal end thereof and the step of positioning the medical implant includes sensing when the leadless pacemaker is in electrical contact with the implantation site within the heart by utilizing the electrode.

7. The method of claim 5, wherein the medical implant is a leadless pacemaker with an electrode extending from the distal end thereof and further comprising the step of testing the implantation site within the heart for suitability by utilizing the electrode prior to distally advancing the collar of the fixation device over the leadless pacemaker.

8. The method of claim 7, wherein the step of testing the implantation site for suitability includes delivering an electrical pulse to the heart via the electrode to test the responsiveness of the implantation site.

9. The method of claim 7, further comprising the step of repositioning the leadless pacemaker if the implantation site is determined to be unacceptable.

10. The method of claim 1, wherein the implant is a leadless pacemaker and the implantation site is in the heart.

11. A system for percutaneously delivering a medical implant to an implantation site, the system comprising:
an outer sheath having a lumen extending there through;
a medical implant slidably received within a distal portion of the outer sheath lumen, wherein a rounded distal end of the medical implant may protrude from a distal end of the outer sheath to form a distal tip of the delivery system; and
a fixation device having an annular collar and an array of self-expanding tines that extend from the collar, wherein the fixation device is slidably mounted on the medical implant such that the fixation device may be distally advanced over the medical implant to deploy the tines from a delivery configuration in which the tines are constrained and substantially straightened by the outer sheath to an expanded configuration in which at least a portion of the tines is released from the outer sheath to radially curve backward towards the collar.

12. The system of claim 11, further comprising an inner pusher slidably disposed within the outer sheath lumen for distally advancing the fixation device over the medical implant.

13. The system of claim 12, wherein the pusher and the collar are releasably coupled together to enable proximal retraction of the fixation device relative to the outer sheath and the medical implant.

14. The system of claim 11, wherein the annular collar of the fixation device encircles the medical implant to be slidable thereover.

15. The system of claim 11, wherein only a distal portion of each tine radially curves backward toward the collar.

16. The system of claim 11, wherein the annular collar engages a stop located on a proximal end of the medical implant when the fixation device is slid there over and wherein straight portions of the tines of the fixation element envelope substantially the entire medical implant when the at least a portion of the tines are in the expanded configuration.

17. The system of claim 11, wherein the medical implant is a leadless pacemaker and an electrode is mounted at the distal end of the medical implant.

18. A medical implant fixation system, the system comprising:
a medical implant percutaneously deliverable and implantable at a vessel wall;
a fixation device having an annular collar and an array of self-expanding tines that distally extend from the collar and radially curve backward towards the collar when deployed, wherein the fixation device is slidably mounted on the medical implant such that the fixation device may be distally advanced over the medical implant to deploy the tines and retain the medical implant to body tissue.

19. The system of claim 18, wherein the annular collar of the fixation device encircles the medical implant to be slidable thereover.

20. The system of claim 18, wherein only a distal portion of each tine radially curves backward towards the collar when deployed.

* * * * *